(12) United States Patent
Hanafusa et al.

(10) Patent No.: US 8,168,135 B2
(45) Date of Patent: May 1, 2012

(54) REACTION CONTAINER PLATE AND ITS REACTION PROCESSING EQUIPMENT

(75) Inventors: Nobuhiro Hanafusa, Kyoto (JP); Koretsugu Ogata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 314 days.

(21) Appl. No.: 12/447,905

(22) PCT Filed: Oct. 23, 2007

(86) PCT No.: PCT/JP2007/070648
§ 371 (c)(1),
(2), (4) Date: Apr. 29, 2009

(87) PCT Pub. No.: WO2008/053751
PCT Pub. Date: May 8, 2008

(65) Prior Publication Data
US 2010/0105130 A1    Apr. 29, 2010

(30) Foreign Application Priority Data

Nov. 1, 2006 (JP) .................................. 2006-297280
Mar. 2, 2007 (JP) .................................. 2007-053374

(51) Int. Cl.
*G01N 31/22* (2006.01)
(52) U.S. Cl. ...................................................... 422/417
(58) Field of Classification Search .................... 422/417
See application file for complete search history.

(56) References Cited

U.S. PATENT DOCUMENTS 6,287,850 B1 * 9/2001 Besemer et al. ........... 435/287.2
6,699,222 B1 * 3/2004 Jones et al. .................... 604/187
6,908,594 B1 * 6/2005 Schaevitz et al. ............. 422/503

(Continued)

FOREIGN PATENT DOCUMENTS

JP          9-238687 A      9/1997

(Continued)

OTHER PUBLICATIONS

Machine English translation of JP2004-325462. Miyake et al. Jun. 3, 2011, 20 pages.*

(Continued)

*Primary Examiner* — Bobby Ramdhanie
(74) *Attorney, Agent, or Firm* — Cheng Law Group, PLLC

(57) ABSTRACT

Intrusion of foreign matters from the outside of a reaction container plate and environmental contamination onto the outside are prevented. The reaction container plate (1) comprises a container base (3) having a reaction container (5), a channel base (11) having an introduction hole (11b) above the reaction container (5) and arranged on the surface of the container base (3), and a channel cover (13) arranged on the channel base (11) in order to form in cooperation with the surface of the channel base, an introduction channel (15) passing above the introduction hole (11b). The channel (13) is formed to be enclosed. The introduction hole (11b) does not allow liquid to pass under an introduction pressure state in the channel (15) where the liquid is introduced into the channel (15) but allows the liquid in the channel (15) to pass to the reaction container (5) side under a pressurized state where the inside of the channel (15) is pressurized higher than the introduction pressure. The channel cover (13) is composed of a flexible member, and, when it is urged to the channel base (11) side after the liquid is introduced into the channel (15), the inside of the channel (15) is brought into a pressurized state and the liquid is passed through the introduction hole (11b) and injected into the reaction container (5).

23 Claims, 9 Drawing Sheets

U.S. PATENT DOCUMENTS

| | | |
|---|---|---|
| 6,989,132 B2 | 1/2006 | Yamamoto |
| 2003/0175947 A1 * | 9/2003 | Liu et al. .................... 435/288.5 |
| 2005/0158213 A1 | 7/2005 | Tsudome et al. |

FOREIGN PATENT DOCUMENTS

| | | | |
|---|---|---|---|
| JP | 2002-504677 | A | 2/2002 |
| JP | 2002-228669 | A | 8/2002 |
| JP | 2003-500205 | A | 1/2003 |
| JP | 3452717 | B2 | 7/2003 |
| JP | 2004-529333 | A | 9/2004 |
| JP | 2004-325462 | A | 11/2004 |
| JP | 2005-512024 | A | 4/2005 |
| JP | 2005-199164 | A | 7/2005 |
| JP | 2006-29485 | A | 2/2006 |
| JP | 2006-197906 | A | 8/2006 |
| JP | 2006-518449 | A | 8/2006 |
| WO | WO-99/42805 | A1 | 8/1999 |
| WO | WO-00/72968 | A1 | 12/2000 |
| WO | WO-02/074438 | A2 | 9/2002 |
| WO | WO-02/074438 | A3 | 9/2002 |
| WO | WO-03/036280 | A2 | 5/2003 |
| WO | WO-2004/062804 | A1 | 7/2004 |

OTHER PUBLICATIONS

International Search Report for the Application No. PCT/JP2007/070648 mailed Jan. 15, 2008.

International Preliminary Report on Patentability for Application No. PCT/JP2007/070648 mailed May 20, 2009.

\* cited by examiner

REACTION CONTAINER PLATE AND ITS REACTION PROCESSING EQUIPMENT

TECHNICAL FIELD

The present invention relates to a reaction container plate suitable for use in various analyses such as bioanalyses, biochemical analyses, and general chemical analyses in the fields of medical care and chemistry, and reaction processing equipment for handling the reaction container plate.

BACKGROUND ART

As small-size reaction apparatuses for use in biochemical analyses and general chemical analyses, micro-multi chamber apparatuses are conventionally used. Examples of such micro-multi chamber apparatuses include microwell reactor plates such as microtiter plates constituted from a flat substrate having a plurality of wells in the surface thereof (see, for example, Patent Document 1).

Patent Document 1: Japanese Patent Application Laid-open No. 2005-177749

Patent Document 2: Japanese Patent No. 3452717

DISCLOSURE OF THE INVENTION

Problem to be Solved by the Invention

In the case of such a conventional microwell reactor plate, the upper surface of the reactor plate is exposed to the atmosphere during use. In this case, there is a fear that foreign matter enters a sample from the outside, and on the other hand, there is also a case where a reaction product contaminates an environment outside the reactor plate.

It is therefore an object of the present invention to provide a reaction container plate capable of preventing the entry of foreign matter from the outside and the contamination of its external environment and reaction processing equipment for handling the reaction container plate.

Means for Solving the Problem

The present invention is directed to a reaction container plate including: a container base constituted from a substrate including a reaction container having an opening on a surface thereof, a channel base provided on the surface of the container base to cover the reaction container and having an introduction hole provided above the reaction container so as to penetrate from a top surface to a back surface thereof, and a channel cover having a hollow space on a surface thereof and provided on the channel base so that the surface having the hollow space faces the channel base to form an introduction channel constituted from the hollow space and the top surface of the channel base, the introduction channel passing above the introduction hole. The introduction channel is hermetically sealable. The introduction hole is designed to prevent a liquid from passing through it when an inside of the introduction channel is at an introduction pressure at which the liquid is introduced into the introduction channel, but permits the liquid to pass through it to inject the liquid contained in the introduction channel into the reaction container when the inside of the introduction channel is pressurized so that a pressure in the introduction channel is made higher than the introduction pressure. The channel cover has a flexible portion in at least part of the corresponding part to the introduction channel. Thereby after the liquid is introduced into the introduction channel, the flexible portion of the channel cover is biased toward the channel base to pressurize the inside of the introduction channel to inject the liquid into the reaction container through the introduction hole.

It is also preferred that the reaction container plate according to the present invention further includes an air vent channel provided so as to communicate with the reaction container.

In this case, it is also preferred that the reaction container plate according to the present invention further includes a hermetically-sealable drain space provided at a position other than a position, at which the reaction container is provided, so as to be connected to the introduction channel and the air vent channel is connected to the drain space.

Further, it is also preferred that the introduction hole has a narrow portion whose inner diameter is smaller than that measured at the top surface of the channel base facing the channel cover.

In this case, the inner diameter of the narrow portion of the introduction hole may be, for example, 1 μm (micrometer) to 2 mm (millimeters).

Further, in the reaction container plate of the present invention, it is also preferred that the container base has two or more of the reaction containers, the introduction hole is provided above each of the reaction containers, and the introduction channel is provided so as to pass above the introduction holes.

Further, it is also preferred that the channel base has a projection projecting from the surface thereof facing the reaction container plate toward the inside of the reaction container, the projection has a proximal end and a distal end narrower than the proximal end, and the introduction hole is provided so as to pass through the projection.

Further, it is also preferred that at least a portion including the introduction hole and its vicinity in the channel base is formed from an elastic member so that the introduction hole is elastically closed enough to prevent the passage of a liquid when the inside of the introduction channel is at the introduction pressure and is elastically opened enough to permit the passage of the liquid when the inside of the introduction channel is pressurized.

Further, it is also preferred that the container base has a sample container for containing a sample liquid.

In this case, the sample container may be hermetically sealed with an elastic member penetrable with a dispensing tool having a sharp tip to form a through hole elastically closable by pulling out the dispensing tool.

In this case, the sample container may previously contain a liquid for sample pretreatment or a reagent.

Further, it is also preferred that the container base has one or more reagent containers previously containing a reagent for use in the reaction of a sample liquid and sealed with a film or one or more reagent containers having a cap openable and closable to inject the reagent. An example of such a film for sealing the reagent container containing a reagent is one penetrable with a dispensing tool having a sharp tip.

Further, it is also preferred that the reaction container is used to perform at least any one of a color reaction, an enzyme reaction, a fluorescence reaction, a chemiluminescence reaction, and a bioluminescence reaction.

In a case where the reaction container plate according to the present invention is intended to perform gene analysis, the reaction container plate preferably has a gene amplification container for performing a gene amplification reaction. Such a gene amplification container preferably has a shape suitable for performing temperature control according to a predetermined temperature cycle. Alternatively, the reaction container may be used as a gene amplification portion. Examples of the gene amplification reaction include PCR and LAMP.

Further, it is also preferred that the reaction container plate according to the present invention further includes a syringe for performing one or both of stirring of a liquid contained in the sample container and introduction of a liquid contained in the sample container into the introduction channel.

In this case, the reaction container plate according to the present invention may further include a switching valve for connecting the syringe to the introduction channel or the sample container.

In this case, the syringe may be used to perform any one or more of stirring of a liquid contained in the sample container, introduction of a liquid contained in the sample container into the introduction channel or the reagent container, and introduction of a liquid contained in the reagent container into the introduction channel.

In this case, the reaction container plate according to the present invention may further include a switching valve for connecting the syringe to the introduction channel, the sample container, or the reagent container.

The switching valve may be, for example, a rotary valve.

In this case, it is preferred that the rotary valve has a port connected to the syringe at its rotation center and the syringe is arranged on the rotary valve.

In a case where the reaction container plate according to the present invention is intended to measure a sample containing a gene, a sample having been subjected to a gene amplification reaction may be introduced into the reaction container plate. Alternatively, the reaction container plate may be configured so that a reagent for gene amplification can be previously contained in the reaction container or a reagent for gene amplification can be dispensed into the reaction container to perform a gene amplification reaction in the reaction container.

Examples of the gene amplification reaction include PCR and LAMP. As a PCR method for amplifying DNA, there has been proposed a method for directly amplifying a target gene contained in a sample such as blood by PCR without pretreatment According to such a nucleic acid synthesis method for amplifying a target gene contained in a gene-containing sample, a gene-including body contained in the gene-containing sample or the gene-containing sample itself is added to a gene amplification liquid so that the pH of the gene amplification liquid is adjusted to 8.5 to 9.5 (25° C.), and as a result, a target gene contained in the gene-containing sample is amplified (see Patent Document 2).

Further, the container base may be made of an optically-transparent material to perform optical measurement from the bottom side of the reaction container.

Further, in a case where a liquid to be introduced into the introduction channel contains a gene, the reaction container may contain a probe that reacts with the gene.

In this case, the probe may be fluorescently-labeled.

The present invention is also directed to reaction processing equipment for handling the reaction container plate according to the present invention, including a biasing system for biasing the flexible portion of the channel cover toward the channel base.

Effects of the Invention

As described above, the reaction container plate according to the present invention includes the container base having a reaction container, the channel base for covering the reaction container, and the channel cover for forming a hermetically-sealable introduction channel together with the channel base, and therefore a liquid introduced into the introduction channel can be injected into the reaction container through the introduction hole by biasing the flexible portion of the channel cover toward the channel base using the reaction processing equipment according to the present invention. This makes it possible to prevent the entry of foreign matter from the outside of the reaction container plate and the contamination of an environment outside the reaction container plate caused by the leakage of a liquid.

Further, by allowing the reaction container plate according to the present invention to further include an air vent channel provided so as to communicate with the reaction container, it is possible to discharge a gas contained in the reaction container into the outside of the reaction container through the air vent channel when a liquid is injected into the reaction container through the introduction hole. This makes it possible to suppress an increase in the pressure in the reaction container resulting from the injection of a liquid into the reaction container, and therefore it is possible to more easily dispense the liquid into the reaction container as compared to a case where the reaction container plate does not have the air vent channel.

Further, by allowing the reaction container plate according to the present invention to further include a hermetically-sealable drain space provided at a position other than a position, at which the reaction container is provided, so as to be connected to the introduction channel and by connecting the air vent channel to the drain space, it is possible to prevent the entry of foreign matter from the outside of the reaction container plate through the air vent channel and the contamination of an environment outside the reaction container plate caused by the leakage of a liquid.

As described above, the reaction container plate according to the present invention has the introduction hole which prevents a liquid from passing through it when the inside of the introduction channel is at the introduction pressure but permits the liquid to pass through it to inject the liquid contained in the introduction channel into the reaction container when the inside of the introduction channel is pressurized to achieve an injection pressure higher than the introduction pressure. Therefore, the inner diameter of the introduction hole needs to be small, but when the introduction hole has a uniform inner diameter, it is necessary to apply a very high injection pressure to dispense a liquid contained in the introduction channel into the reaction container. Particularly, when the contact angle of the liquid with respect to the channel base is large (e.g., 90° or more), it is necessary to apply a high injection pressure.

Therefore, by allowing the introduction hole to have a narrow portion whose inner diameter is smaller than that of the introduction hole measured at the top surface of the channel base, it is possible for the introduction hole to have a relatively large inner diameter at the top surface of the channel base facing the channel cover. This makes it possible to dispense a liquid into the reaction container at a lower injection pressure as compared to a case where the introduction hole has a uniform inner diameter.

Further, in the reaction container plate of the present invention, by allowing the container base to have the two or more reaction containers, providing the injection hole above each of the reaction containers, and allowing the introduction channel to pass above the introduction holes, it is possible to inject a liquid into the reaction containers at the same time.

Further, by allowing the channel base to have a projection projecting from the surface thereof facing the reaction container plate toward the inside of the reaction container, allowing the projection to have a proximal end and a distal end narrower than the proximal end, and allowing the introduction hole to pass through the projection, it is possible to easily drop a liquid into the reaction container when the liquid is injected into the reaction container through the introduction hole.

Further, by forming at least a portion including the introduction hole and its vicinity in the channel base from an elastic member so that the introduction hole is elastically closed enough to prevent the passage of a liquid when the inside of the introduction channel is at the introduction pressure but is elastically opened enough to permit the passage of the liquid when the inside of the introduction channel is pressurized, it is possible to reliably inject the liquid contained in the introduction channel into the reaction container when the inside of the introduction channel is pressurized.

Further, by allowing the container base to have a sample container for containing a sample liquid, it is possible to eliminate the necessity to separately prepare a container for containing a sample.

In this case, by hermetically sealing the sample container with an elastic member penetrable with a dispensing tool having a sharp tip to form a through hole elastically closable by pulling out the dispensing tool, it is possible to inject a sample liquid into the sample container through the through hole formed in the elastic member and to prevent the leakage of the sample liquid into the outside of the sample container even after the dispensing tool is pulled out.

In this case, by allowing the sample container to previously contain a liquid for sample pretreatment or a regent, it is possible to eliminate the necessity to dispense a liquid for sample pretreatment or a reagent into the sample container.

Further, by allowing the container base to have one or more reagent containers containing a reagent for use in the reaction of a sample liquid and sealed with a film, it is possible to eliminate the necessity to separately prepare a container for containing the reagent.

Further, by allowing the container base to have a gene amplification container for performing a gene amplification reaction, it is possible to amplify a gene by a gene amplification reaction such as PCR or LAMP in the reaction container plate even when the amount of a target gene contained in a sample liquid is very small. This makes it possible to improve the accuracy of gene analysis.

Further, by allowing the reaction container plate according to the present invention to further include a syringe for performing one or both of stirring of a liquid contained in the sample container and introduction of a liquid contained in the sample container into the introduction channel, it is possible to eliminate the necessity to separately prepare a syringe.

In this case, by further providing a switching valve for connecting the syringe to the introduction channel or the sample container, it is possible to perform stirring of a liquid contained in the sample container and introduction of a liquid contained in the sample container into the introduction channel with the syringe and the switching valve.

Further, by allowing the container base to have a reagent container containing a reagent for use in the reaction of a sample liquid and sealed with a film and by allowing the syringe to perform one or more of stirring of a liquid contained in the sample container, introduction of a liquid contained in the sample container into the introduction channel or the reagent container, and introduction of a liquid contained in the reagent container into the introduction channel, it is possible to eliminate the necessity to separately prepare a syringe.

In this case, by further providing a switching valve for connecting the syringe to the introduction channel, the sample container, or the reagent container, it is possible to perform stirring of a liquid contained in the sample container, introduction of a liquid contained in the sample container into the introduction channel or the reagent container, and introduction of a liquid contained in the reagent container into the introduction channel.

The switching valve may be a rotary valve. In this case, by allowing the rotary valve to have a port connected to the syringe at its rotation center, it is possible to simplify the channel configuration of the reaction container plate.

Further, by allowing the rotary valve to have a port connected to the syringe at its rotation center and by arranging the syringe on the rotary valve, it is possible to shorten or eliminate a channel between the port and the syringe, thereby simplifying the structure of the reaction container plate. In addition, it is also possible to effectively utilize an area on the switching valve, thereby reducing the two-dimensional size of the reaction container plate as compared to a case where the syringe is arranged in an area other than an area on the switching valve.

Further, in a case where the reaction container plate is intended to measure a sample containing a gene, the sample introduced into the reaction container plate and then injected into the reaction container can be treated in a closed system, thereby preventing the contamination of an environment outside the reaction container plate and the contamination of the sample with foreign matter coming from the outside.

Further, by making the container base of an optically-transparent material so that optical measurement can be performed from the bottom side of the reaction container, it is possible to perform optical measurement without transferring a liquid contained in the reaction container into another container.

Figure 1A:
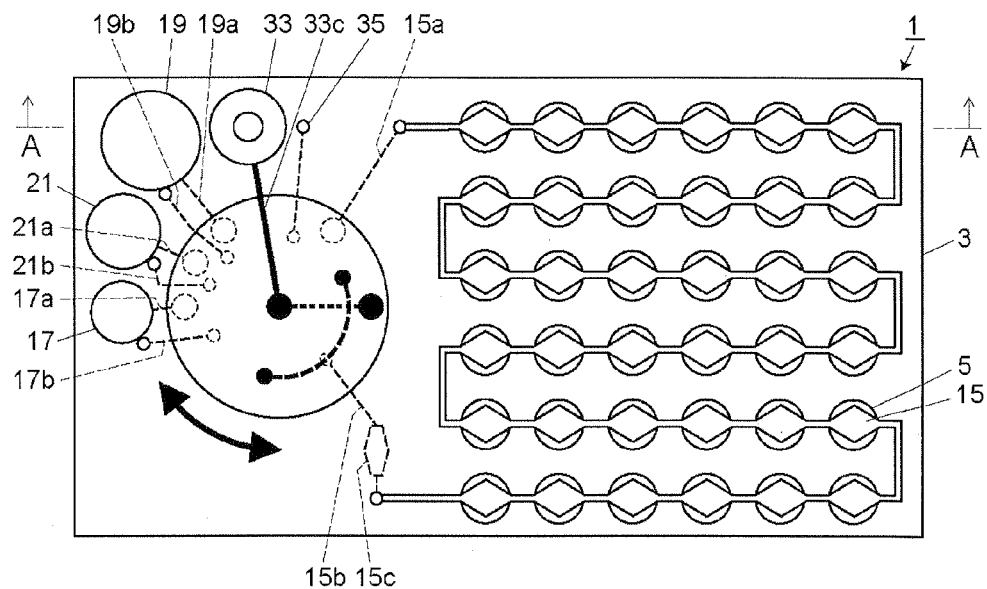
FIG. 1A is a plan view of one embodiment of a reaction container plate.

DESCRIPTION OF THE REFERENCE NUMERALS 1 reaction container plate
3 container base
5 reaction container
11 channel base
11a projection
11b introduction hole
12 introduction hole
12a channel
12b channel
13 channel cover
15 introduction channel
17 sample container
19 reagent container
33 syringe
47 switching valve
59 channel base
60 introduction hole
60a channel
60b channel

BEST MODES FOR CARRYING OUT THE INVENTION

Figure 1B:
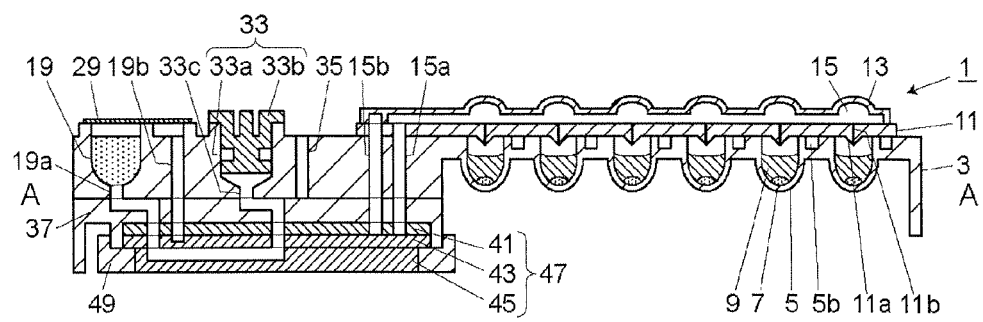
FIG. 1B is a sectional view taken along the A-A line in FIG. 1A with a sectional view of a switching valve.
Figure 2:
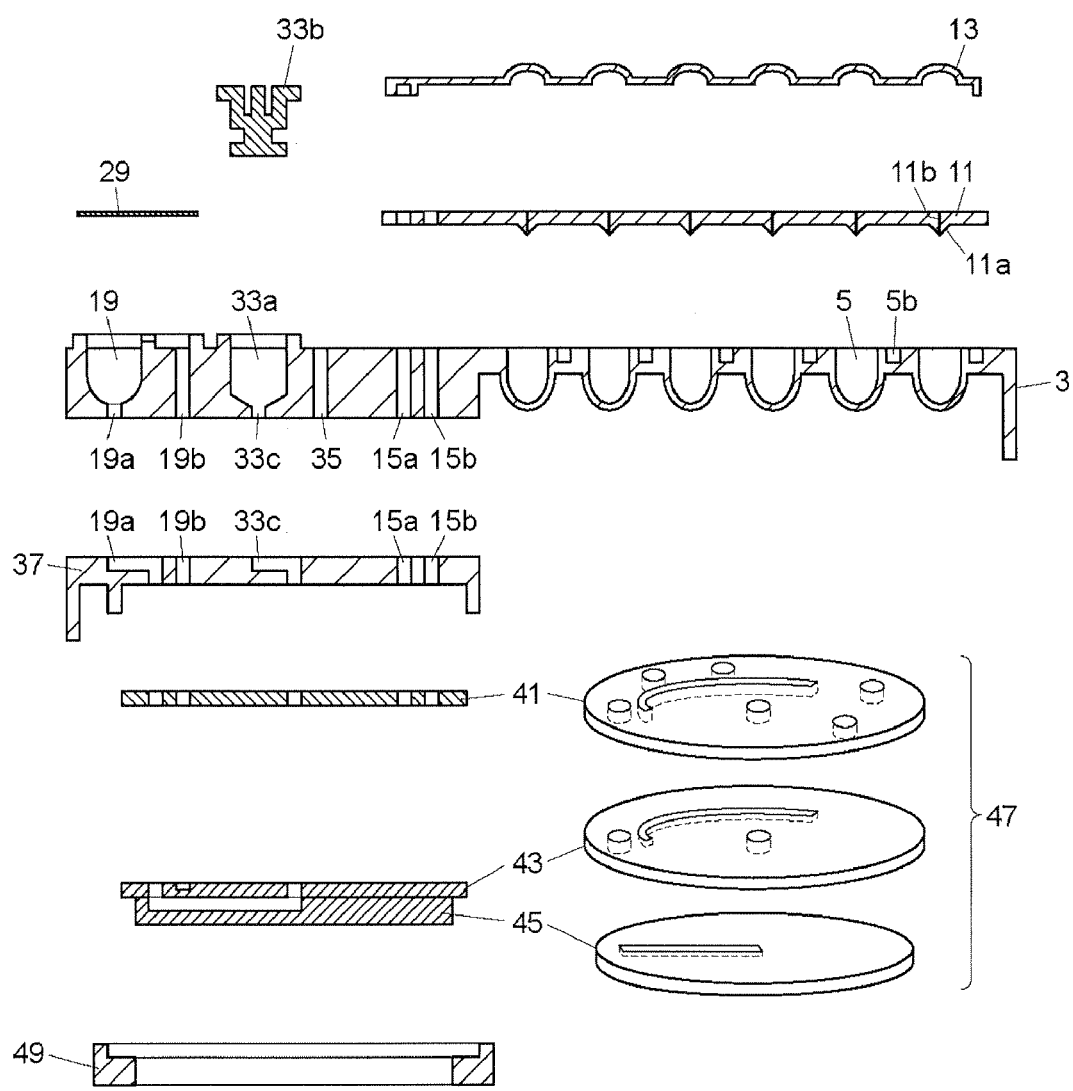
FIG. 2 shows an exploded sectional view of the reaction container plate and an exploded perspective view of the switching valve.
Figure 3:
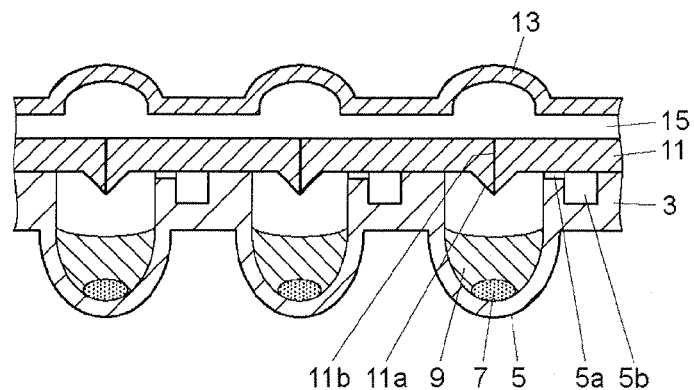
FIG. 3 is an enlarged sectional view of reaction containers of the reaction container plate.
Figure 4A:
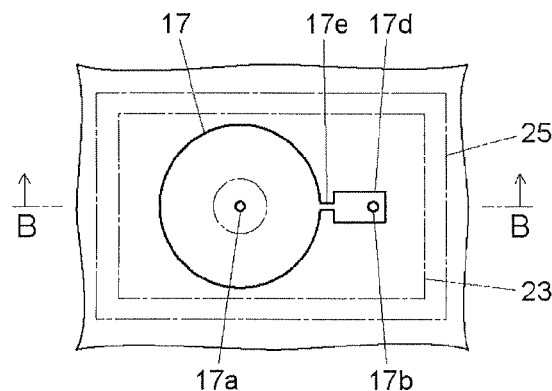
FIG. 4A is an enlarged plan view of a sample container of the reaction container plate.
Figure 4B:
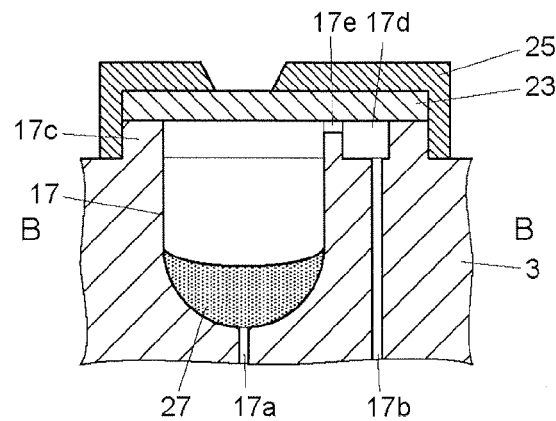
FIG. 4B is a sectional view taken along the B-B line in FIG. 4A.
Figure 5A:
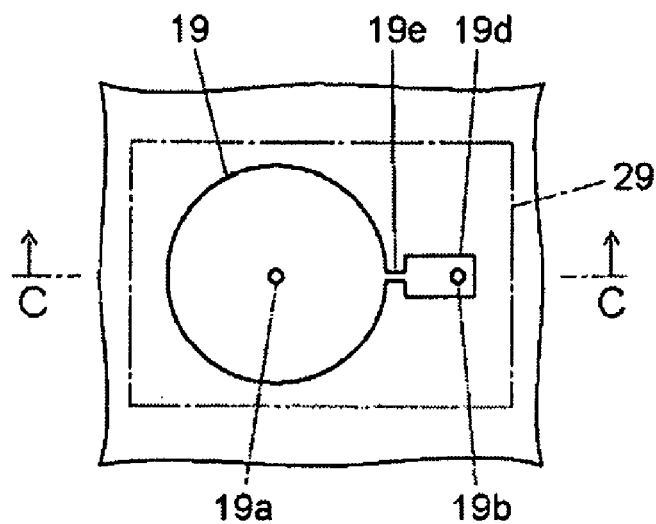
FIG. 5A is an enlarged plan view of a reagent container of the reaction container plate.
Figure 5B:
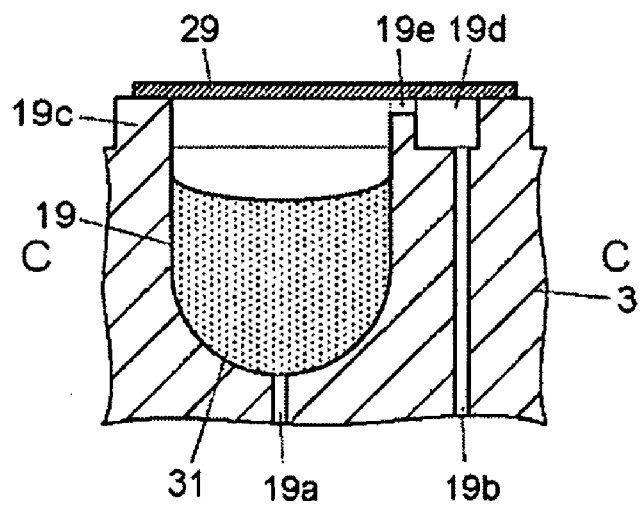
FIG. 5B is a sectional view taken along the C-C line in FIG. 5A.

FIG. 1A is a plan view of one embodiment of a reaction container plate, and FIG. 1B is a sectional view taken along the A-A line in FIG. 1A with a sectional view of a switching valve. FIG. 2 shows an exploded sectional view of the reaction container plate and an exploded perspective view of the switching valve. FIG. 3 is an enlarged sectional view of reaction containers of the reaction container plate. FIG. 4A is an enlarged plan view of a sample container, and FIG. 4B is a sectional view taken along the B-B line in FIG. 4A. FIG. 5A is an enlarged plan view of a reagent container, and FIG. 5B is a sectional view taken along the C-C line in FIG. 5A.

Hereinbelow, one embodiment of a reaction container plate will be described with reference to FIGS. 1 to 5.

A reaction container plate 1 has a container base 3 including a plurality of reaction containers 5 each having an opening in one surface thereof. In this embodiment, the reaction containers 5 are arranged in a matrix of 6 rows and 6 columns, and contain a reagent 7 and a wax 9.

The material of the container base 3 including the reaction containers 5 is not particularly limited. When the reaction container plate 1 is intended to be disposable, the container base 3 is preferably made of a cheaply-available material. Preferred examples of such a cheaply-available material include resin materials such as polypropylene and polycarbonate. When the reaction container plate 1 is intended to perform absorbance detection, fluorescence detection, chemiluminescence detection, or bioluminescence detection in the reaction containers 5 or a detection portion separately provided, the container base 3 is preferably made of an optically-transparent resin so that optical detection can be performed from the bottom side of the container base 3. Particularly, when the reaction container plate 1 is intended to perform fluorescence detection, the container base 3 is preferably made of an optically-transparent resin with low autofluorescence (which means that the amount of fluorescence emitted from the resin itself is small) such as polycarbonate. The thickness of the container base 3 is 0.2 to 4.0 mm, preferably 1.0 to 2.0 mm. From the viewpoint of low autofluorescence, the container base 3 of the reaction container plate 1 intended to perform fluorescence detection preferably has a small thickness.

Referring to FIGS. 1 and 3, a channel base 11 (not shown in FIG. 1A) is provided on the container base 3 so as to cover an area where the reaction containers 5 are arranged. The channel base 11 is made of an elastic material such as silicone rubber or PDMS (polydimethylsiloxane). The thickness of the channel base 11 is, for example, 1.0 mm. The channel base 11 has projections 11a each of which projects from the surface thereof facing the container base 3 toward the inside of each of the reaction containers 5. Each of the projections 11a has a substantially trapezoidal section having a proximal end and a distal end narrower than the proximal end. The proximal end of the projection 11a has a width of, for example, 1.0 to 2.8 mm and the distal end of the projection 11a has a width of, for example, 0.2 to 0.5 mm.

The channel base 11 has introduction holes 11b each of which is provided at a position where the projection 11a is provided. Each of the introduction holes 11b penetrates the channel base 11 from the distal end of the projection 11a to the surface of the channel base 11 opposite to the surface having the projections 11a. The introduction holes 11b are closed enough to prevent the passage of a liquid due to the elasticity of a material constituting the channel base 11.

A channel cover 13 (not shown in FIG. 1A) is provided on the channel base 11. The channel cover 13 has a thickness of, for example, 0.2 to 0.5 mm and is made of, for example, a flexible material such as silicone rubber or PDMS. The channel cover 13 has recesses provided in the surface thereof facing the channel base 11. These recesses and the surface of the channel base 11 form an introduction channel 15. The introduction channel 15 is provided so as to pass above all the 36 introduction holes 11b. Further, the introduction channel 15 has wider portions at positions corresponding to the reaction containers 5.

As shown in FIG. 3, air vent channels 5a are provided in the surface of the container base 3 within the area where the reaction containers 5 are arranged. Each of the air vent channels 5a communicates with each of the reaction containers 5. Further, airspaces 5b are provided so as to extend in the direction perpendicular to the sheet of paper. Each of the airspaces 5b is constituted from a groove communicating with the air vent channels 5a. The airspaces 5b communicate with each other in an area not shown. The air vent channels 5a and the airspaces 5b are covered with the channel base 11. Each of the air vent channels 5a has a width of, for example, 5 to 500 μm and a depth of, for example, 5 to 500 μm.

Referring to FIGS. 1 and 4, a sample container 17 and reagent containers 19 and 21 are provided in the surface of the container base 3 at positions outside the area where the reaction containers 5 are arranged.

A sample channel 17a and a sample air vent channel 17b are provided near the sample container 17 in the container base 3. The sample channel 17a penetrates the container base 3 from the bottom of the sample container 17 to the back surface of the container base 3. The sample air vent channel 17b penetrates the container base 3 from the top surface to the back surface thereof. A bump 17c is provided on the container base 3 so as to surround the opening of the sample container 17. A sample airspace 17d constituted from a through hole is provided in the bump 17c so as to be located above the air vent channel 17b. A sample air vent channel 17e is provided in the surface of the bump 17c to allow the sample container 17 to communicate with the sample airspace 17d. The air vent channel 17e has a width of, for example, 5 to 200 µm and a depth of, for example, 5 to 200 µm. A septum 23 is provided on the bump 17c so as to cover the sample container 17 and the airspace 17d. The septum 23 is made of, for example, silicone rubber or PDMS. Therefore, the septum 23 is penetrable with a dispensing tool having a sharp tip to form a through hole elastically closable by pulling out the dispensing tool. A septum stopper 25 is provided on the septum 23 to fix the septum 23. The septum stopper 25 has an opening at a position corresponding to the sample container 17. In this embodiment, a regent 27 is previously contained in the sample container 17.

A reagent channel 19a and a reagent air vent channel 19b are provided near the reagent container 19 in the container base 3. The reagent channel 19a penetrates the container base 3 from the bottom of the reagent container 19 to the back surface of the container base 3. The reagent air vent channel 19b penetrates the container base 3 from the top surface to the back surface thereof. A bump 19c is provided on the container base 3 so as to surround the opening of the reagent container 19. A reagent airspace 19d constituted from a through hole is provided in the bump 19c so as to be located above the air vent channel 19b. A reagent air vent channel 19e is provided in the surface of the bump 19c to allow the reagent container 19 to communicate with the reagent airspace 19d. The air vent channel 19e has a width of, for example, 5 to 200 µm and a depth of, for example, 5 to 200 µm. A film 29 made of, for example, aluminum is provided on the bump 19c so as to cover the reagent container 19 and the airspace 17d. A reagent 31 is contained in the reagent container 19.

Although not shown in detail, the reagent container 21 has the same structure as the reagent container 19. More specifically, a reagent container channel 21a and a reagent container air vent channel 21b are provided near the reagent container 21 in the container base 3. The reagent container channel 21a penetrates the container base 3 from the bottom of the reagent container 21 to the back surface of the container base 3. The reagent container air vent channel 21b penetrates the container base 3 from the top surface to the back surface thereof. A bump having an air vent channel and an airspace is provided on the container base 3 so as to surround the opening of the reagent container 21. A film made of, for example, aluminum is provided on the bump.

Referring to FIGS. 1 and 2, a syringe 33 is provided in the surface of the container base 3 at a position outside the area where the reaction containers 5 are arranged and other than the positions where the containers 17, 19, and 21 are provided. The syringe 33 includes a cylinder 33a and a plunger 33b. The cylinder 33a is provided in the container base 3, and the plunger 33b is arranged in the cylinder 33a. Further, a cylinder channel 33c is provided so as to penetrate the container base 3 from the bottom of the cylinder 33a to the back surface of the container base 3.

An introduction channel 15a, a drain channel 15b, and an air vent channel 35 are also provided in the container base 3 so as to penetrate the container base 3 from the top surface to the back surface thereof. The introduction channel 15a is connected to one end of the introduction channel 15, which is provided between the channel base 11 and the channel cover 13, through a through hole provided in the channel base 11. The drain channel 15b is connected to the other end of the introduction channel 15 through another through hole provided in the channel base 11. In the drain channel 15b, a drain space 15c is provided. The airspaces 5b described above with reference to FIG. 3 are connected to the drain space 15c.

A container bottom 37 is attached to the back surface of the container base 3 at a position outside the area where the reaction containers 5 are arranged. The container bottom 37 is provided to lead the channels 15a, 15b, 17a, 17b, 19a, 19b, 21a, 21b, 33c, and 35 to their respective predetermined port positions.

A rotary switching valve 47 is provided on the surface of the container bottom 37 not facing the container base 3. The rotary switching valve 47 includes a disk-shaped sealing plate 41, a rotor upper 43, and a rotor base 45, and is attached to the container bottom 37 by means of a lock 49.

The sealing plate 41 has four through holes provided on a concentric circle located near the outer edge thereof so as to correspond to the channels 15a, 17a, 19a, and 21a, one through groove provided on a concentric circle inside the concentric circle, on which the four through holes are provided, so as to correspond to the channels 15b, 17b, 19b, 21b, and 35, and a through hole provided at the center thereof so as to communicate with the syringe channel 33c.

The rotor upper 43 has one through hole to be connected to any one of the channels 15a, 17a, 19a, and 21a, a groove provided in the surface thereof so as to correspond to the through groove provided in the sealing plate 41, and a through hole provided at the center thereof so as to communicate with the syringe channel 33c.

The rotor base 45 has a groove provided in the surface thereof to connect the two through holes provided at the center and periphery of the rotor upper 43 to each other.

When the switching valve 47 is rotated, the syringe channel 33c is connected to any one of the channels 15a, 17a, 19a, and 21a, and at the same time, the air vent channel 35 is connected to any one or more of the channels 15b, 17b, 19b, and 21b.

The switching valve 47 shown in FIG. 1A is in its initial state where the syringe channel 33c is not connected to any of the channels 15a, 17a, 19a, and 21a and the air vent channel 35 is not connected to any of the channels 15b, 17b, 19b, 21b, and 35 either. The channels 15a and 15b are not connected to any of the ports, and therefore the introduction channel 15 is hermetically sealed.

Figure 6:
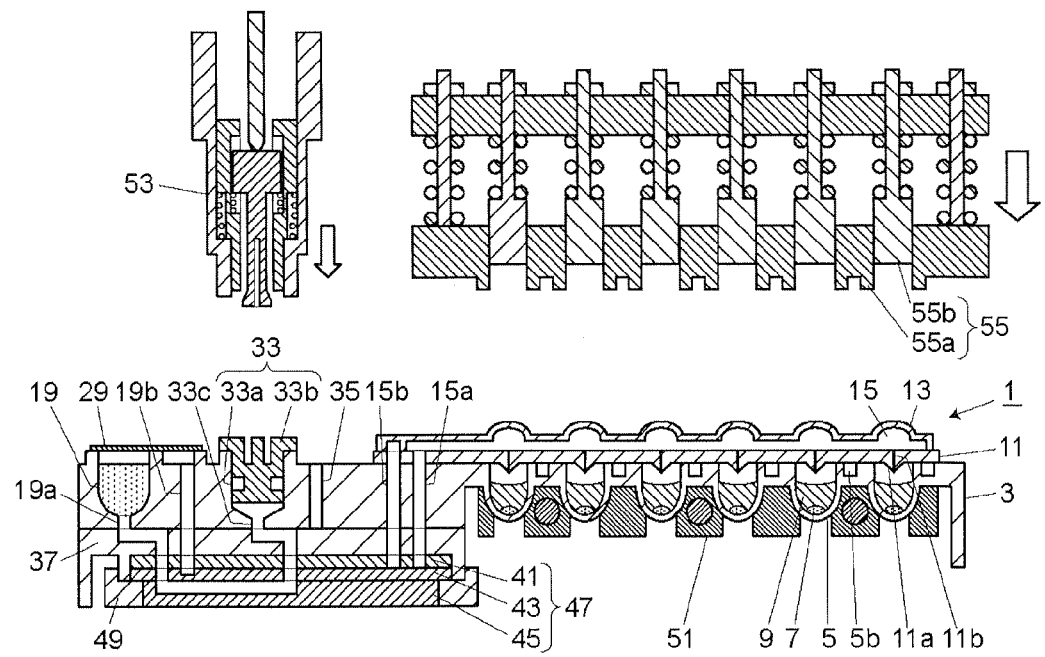
FIG. 6 is a sectional view of one embodiment of reaction processing equipment with a sectional view of the reaction container plate.

FIG. 6 is a sectional view of reaction processing equipment for handling the reaction container plate shown in FIG. 1 with a sectional view of the reaction container plate. The reaction container plate 1 shown in FIG. 6 has the same structure as that shown in FIG. 1, and therefore the description of the reaction container plate 1 is omitted.

The reaction processing equipment includes a temperature control system 51, a driving unit 53, and a biasing system 55. The temperature control system 51 is provided to control the temperature of the reaction containers 5, the driving unit 53 is provided to drive the syringe 33, and the biasing system 55 is provided to bias the channel cover 13 toward the channel base 11. The biasing system 55 has a first unit 55a and a second unit 55b. The first unit 55a is provided to bias the channel cover 13 toward the channel base 11 at positions around the reaction containers 5, and the second unit 55b is provided to bias the channel cover 13 toward the channel base 11 at positions corresponding to the reaction containers 5. Further, the reaction processing equipment includes also a switching valve driving unit (not shown).

Figure 7:
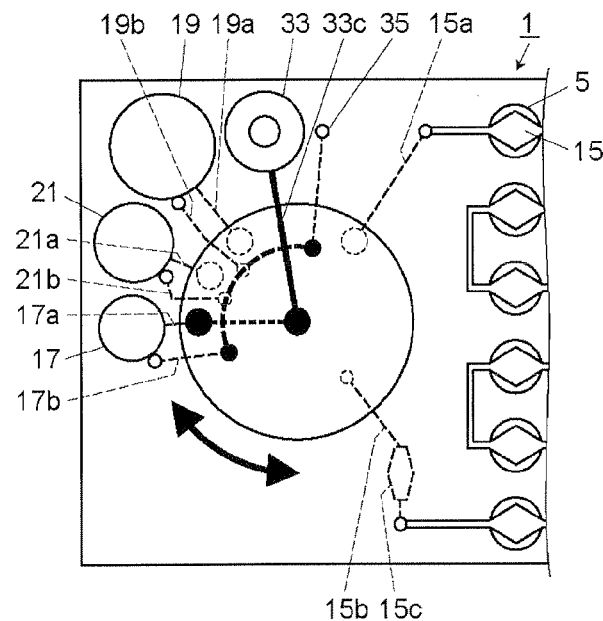
FIG. 7 is a plan view showing channel connection using the switching valve for illustrating operation to introduce a sample liquid from the sample container into an introduction channel.
Figure 8:
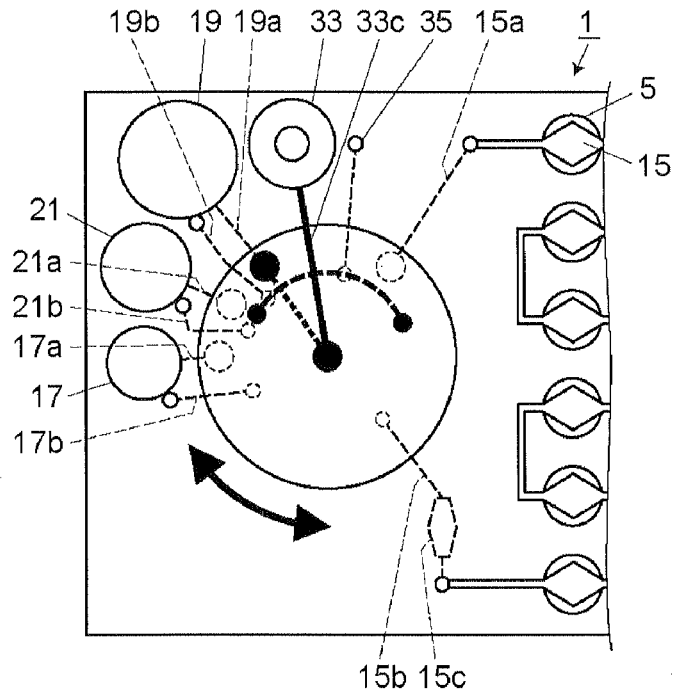
FIG. 8 is a plan view showing channel connection using the switching valve for illustrating operation subsequent to the operation shown in FIG. 7.
Figure 9:
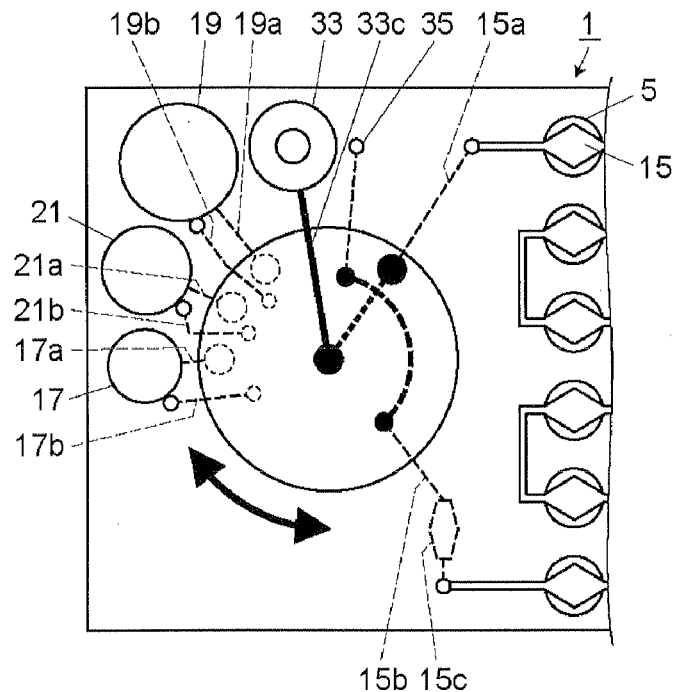
FIG. 9 is a plan view showing channel connection using the switching valve for illustrating operation subsequent to the operation shown in FIG. 8.

FIGS. 7 to 9 are plan views showing channel connection using the switching valve 47 for illustrating operation to introduce a sample liquid from the sample container 17 into the introduction channel 15. The operation will be described with reference to FIG. 1 and FIGS. 6 to 9.

The driving unit 53 is attached to the syringe 33.

As shown in FIG. 7, the switching valve 47 in its initial state shown in FIG. 1A is rotated to connect the sample channel 17a to the syringe channel 33c and connect the air vent channel 17b to the air vent channel 35. At this time, the air vent channels 19b and 21b are also connected to the air vent channel 35.

A dispensing tool having a sharp tip (not shown) is allowed to penetrate the septum 23 provided on the sample container 17 to dispense a sample liquid into the sample container 17. After dispensing the sample liquid, the dispensing tool is pulled out. A through hole formed in the septum 23 by allowing the dispensing tool to penetrate the septum 23 is closed by pulling out the dispensing tool due to the elasticity of the septum 23.

The syringe 33 is slid to mix the sample liquid and the reagent 27 contained in the sample container 17 to obtain a mixed liquid. Then, the mixed liquid contained in the sample container 17 is sucked into a channel provided in the switching valve 47, the syringe channel 33c, and the syringe 33. At this time, the pressure in the sample container 17 is not reduced because the sample container 17 is connected to the air vent channel 35 through the air vent channel 17b and the switching valve 47.

As shown in FIG. 8, the switching valve 47 is rotated to connect the reagent channel 19a to the syringe channel 33c and connect the air vent channel 19b to the air vent channel 35. The mixed liquid sucked into the channel provided in the switching valve 47, the syringe channel 33c, and the syringe 33 is dispensed into the reagent container 19 to further mix the mixed liquid with the reagent 31. The thus obtained mixed liquid is sucked into the channel provided in the switching valve 47, the syringe channel 33c, and the syringe 33. It is to be noted that during the operation described here, the reagent container 21 is not used.

As shown in FIG. 9, the switching valve 47 is rotated to connect the introduction channel 15a to the syringe channel 33c and connect the drain channel 15b to the air vent channel 35. This allows the syringe 33, the introduction channels 15a and 15, the drain channel 15b, and the air vent channel 35 to communicate with each other. The mixed liquid sucked into the channel provided in the switching valve 47, the syringe channel 33c, and the syringe 33 is dispensed into the introduction channel 15 through the introduction channel 15a. The mixed liquid that has reached the drain channel 15b through the introduction channel 15 is stored in the drain space 15c.

Figure 10A:
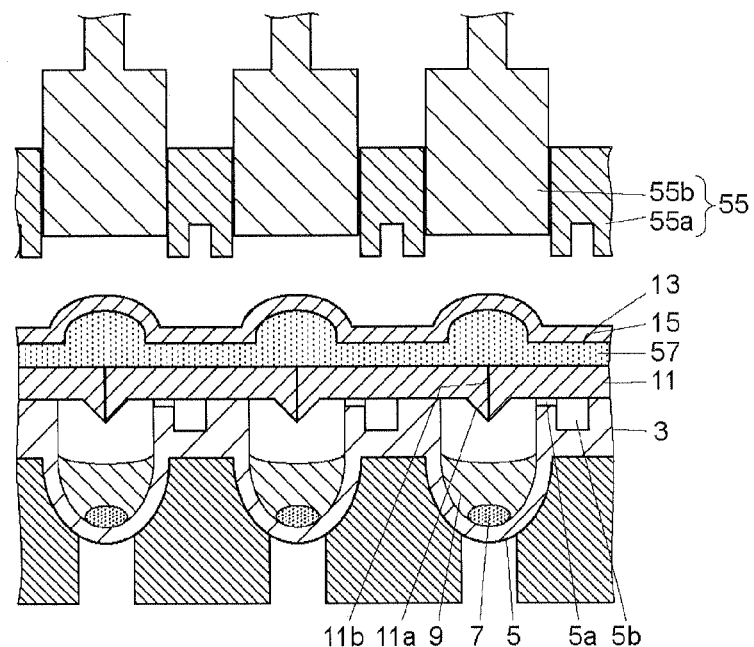
FIG. 10A is an enlarged sectional view of the reaction containers and their vicinity showing a state where a liquid is introduced into the introduction channel, which is used for illustrating operation to be performed after the liquid is introduced into the introduction channel.
Figure 10B:
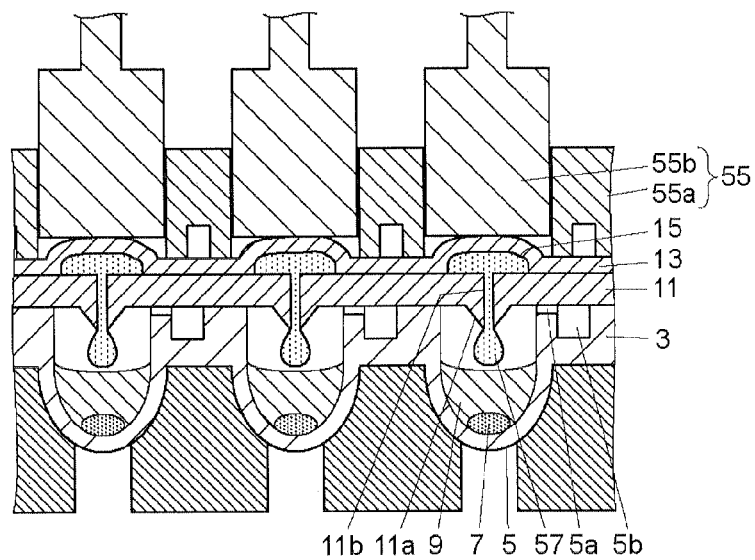
FIG. 10B is an enlarged sectional view of the reaction containers and their vicinity showing a state where the liquid is dispensed into the reaction containers, which is used for illustrating operation to be performed after the liquid is introduced into the introduction channel.

FIGS. 10A and 10B are enlarged sectional views of the reaction containers and their vicinity for illustrating operation to be performed after a liquid is introduced into the introduction channel 15. More specifically, FIG. 10A is an enlarged sectional view showing a state where a liquid is introduced into the introduction channel 15, and FIG. 10B is an enlarged sectional view showing a state where the liquid is dispensed into the reaction containers.

As shown in FIG. 10A, a mixed liquid 57 is introduced into the introduction channel 15.

As shown in FIG. 10B, when the biasing system 55 is moved toward the reaction container plate 1 while the switching valve 47 is kept in a state shown in FIG. 9, the first unit 55a located closer to the reaction container plate 1 than the second unit 55b presses the channel cover 13 against the channel base 11 at positions around the reaction containers 5. This creates enclosed introduction channel spaces containing the mixed liquid 57 above the reaction containers 5 and the introduction holes 11b.

When the biasing system 55 is further moved toward the reaction container plate 1, the channel cover 13 is biased toward the channel base 11 by the second unit 55b at positions corresponding to the enclosed introduction channel spaces. This increases the pressure in the enclosed introduction channel spaces so that the introduction holes 11b are elastically opened and then the mixed liquid 57 is dispensed into the reaction containers 5. At this time, the reaction containers 5 are connected to the air vent channel 35 through the air vent channels 5a, the airspaces 5b, the drain channel 15b, and the drain space 15c. This makes it possible to transfer a gas contained in the reaction containers 5 to the air vent channel 5a side. Therefore, an increase in the pressure in the reaction containers 5 can be suppressed, thereby allowing the mixed liquid 57 to be easily dispensed into the reaction containers 5.

When the biasing system 55 is moved so as to separate from the reaction container plate 1, the pressure in the introduction channel 15 is reduced so that the introduction holes 11b are elastically closed. Then, the switching valve 47 is rotated to return to its initial state shown in FIG. 1A to hermetically seal the introduction channel 15. By doing so, it is possible to prevent the leakage of the mixed liquid 57 and a liquid contained in the reaction containers 5 into the outside of the reaction container plate 1.

The reaction containers 5 are heated by the temperature control system 51 to melt the wax 9 to react the mixed liquid 57 with the reagent 7. It is to be noted that the reaction containers 5 may be heated by the temperature control system 51 before the mixed liquid 57 is dispensed into the reaction containers 5 to melt the wax 9. In this case, the wax 9 is in a molten state when the mixed liquid 57 is dispensed into the reaction containers 5.

Figure 11A:
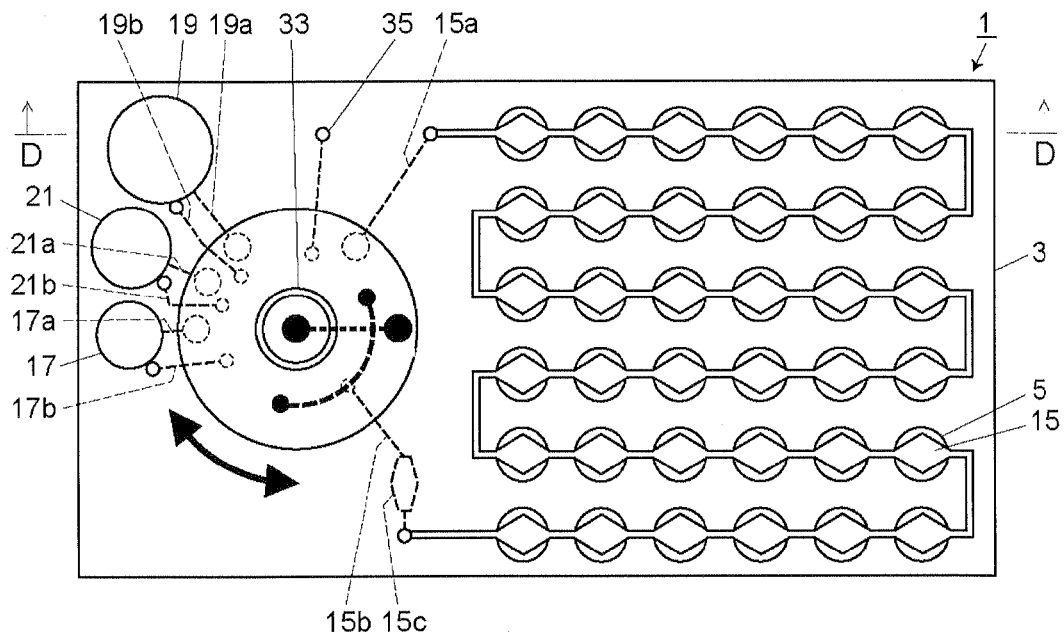
FIG. 11A is a plan view of another embodiment of the reaction container plate.
Figure 11B:
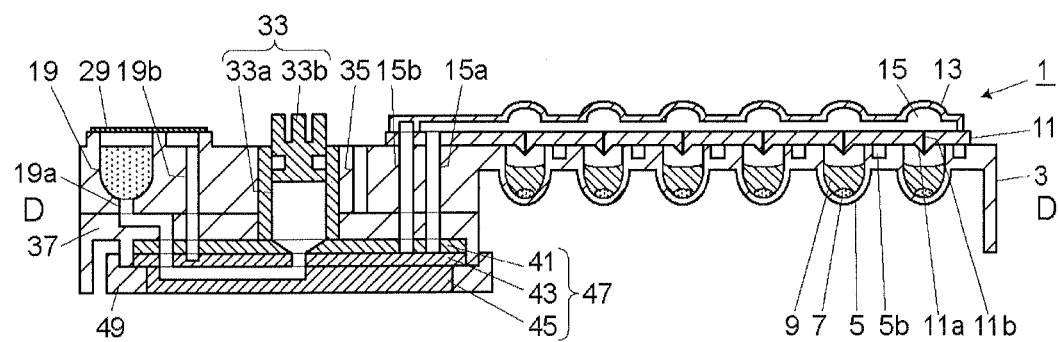
FIG. 11B is a sectional view taken along the D-D line in FIG. 11A.

FIG. 11A is a plan view of another embodiment of the reaction container plate, and FIG. 11B is a sectional view taken along the D-D line in FIG. 11A with a sectional view of a switching valve. It is to be noted that in FIG. 1 and FIG. 11, the same reference numerals indicate parts having the same function, and the description of these parts will be omitted.

The reaction container plate shown in FIG. 11 is different from the reaction container plate shown in FIG. 1 in that the syringe 33 is arranged on the switching valve 47. This makes it possible to eliminate the channel between the syringe 33 and the switching valve 47, thereby simplifying the structure of the reaction container plate. Further, it is also possible to effectively utilize an area on the switching valve 47, thereby reducing the two-dimensional size of the reaction container plate 1 as compared to a case where the syringe 33 is arranged in an area other then an area on the switching valve 47.

Figure 12:
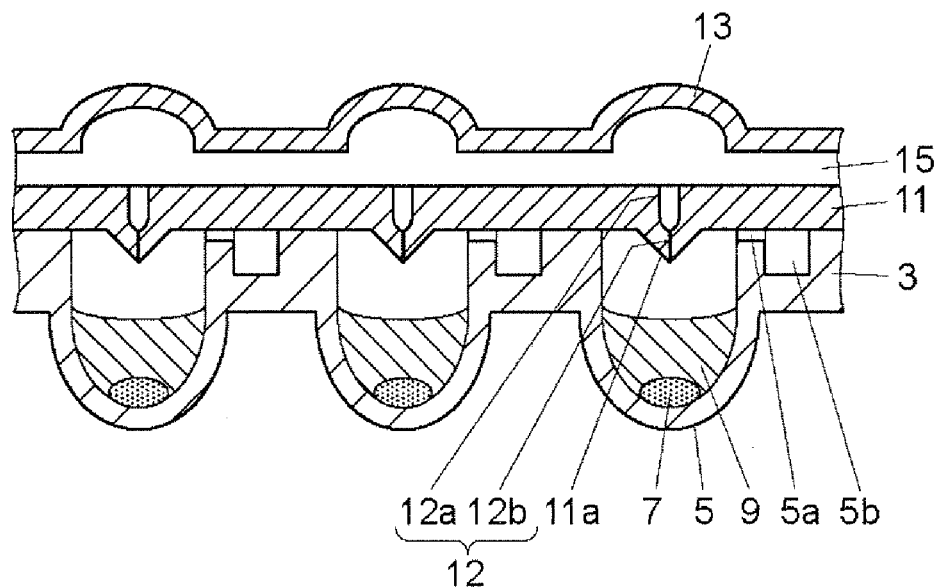
FIG. 12 is an enlarged sectional view of reaction containers and their vicinity of yet another embodiment of the reaction container plate.

FIG. 12 is an enlarged sectional view of reaction containers and their vicinity of yet another embodiment of the reaction container plate. The yet another embodiment is the same as the embodiment described above with reference to FIGS. 1 to 5 except for the shape of the introduction holes provided in the channel base.

As shown in FIG. 12, the channel base 11 has introduction holes 12. Each of the introduction holes 12 includes a channel 12a and a channel 12b. The channel 12a is provided in the surface of the channel base 11 facing the channel cover 13, and the channel 12b is provided so as to penetrate the channel base 11 from the bottom of the channel 12a to the distal end of the projection 11a. The inner diameter of the channel 12b is smaller than that of the channel 12a measured at the surface of the channel base 11. The channel 12b is closed enough to prevent the passage of a liquid due to the elasticity of a material constituting the channel base 11. The inner diameter of the channel 12a measured at the surface of the channel base 11 is, for example, 100 μm to 2 mm.

Such introduction holes 12 can have a relatively large inner diameter at the surface of the channel base 11 facing the channel cover 13, and therefore it is possible to dispense a liquid into the reaction containers 5 at a lower injection pressure as compared to a case where the introduction holes have a uniform inner diameter.

As in the case shown in FIG. 10B, the channels 12b are elastically opened when a liquid is dispensed into the reaction containers 5.

Figure 13:
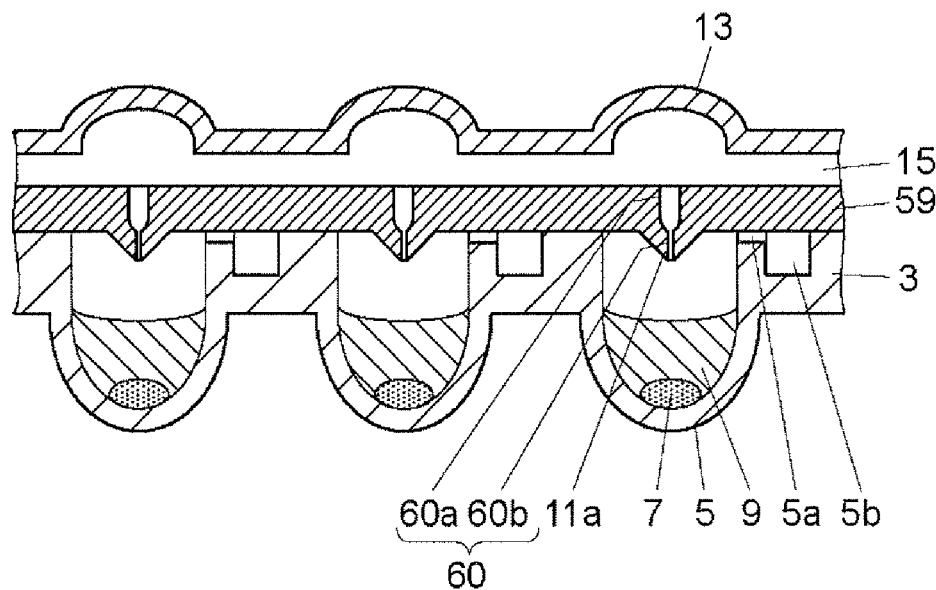
FIG. 13 is an enlarged sectional view of reaction containers and their vicinity of yet another embodiment of the reaction container plate.

FIG. 13 is an enlarged sectional view of reaction containers and their vicinity of yet another embodiment of the reaction container plate. This embodiment shown in FIG. 13 is the same as the embodiment described above with reference to FIGS. 1 to 5 except for the material of the channel base and the shape of the introduction holes.

A channel base 59 is made of a hard material such as PMMA (acrylic), PC (polycarbonate), COC (cycloolefin copolymer), or COP (cycloolefin polymer). The channel base 59 has introduction holes 60, each of which is provided at a position where the projection 11a is provided. Each of the introduction holes 60 penetrates the channel base 59 from the distal end of the projection 11a to the surface of the channel base 59 opposite to the surface having the projections 11a. Each of the introduction holes 60 includes a channel 60a and a channel 60b. The channel 60a is provided in the surface of the channel base 59 facing the channel cover 13, and the channel 60b is provided so as to penetrate the channel base 59 from the bottom of the channel 60a to the distal end of the projection 11a. The channel 60b has an inner diameter of, for example, 1 μm to 2 mm, which is smaller than that of the channel 60a measured at the surface of the channel base 59 (e.g., 100 μm to 3 mm).

The channel 60b has a size that prevents a liquid from passing through it when the inside of the introduction channel 15 is at an introduction pressure at which the liquid is introduced into the introduction channel 15 but permits the liquid to pass through it to inject the liquid contained in the introduction channel 15 into the reaction container 5 when the inside of the introduction channel 15 is pressurized so that a pressure in the introduction channel 15 is made higher than the introduction pressure. For example, in a case where a liquid to be introduced into the introduction channel 15 is hydrophilic, it is possible to more reliably prevent the liquid from being injected into the reaction containers 5 through the channels 60b under the introduction pressure by making the inner wall of the channels 60b of a hydrophobic material. However, the channel 60b is not limited to one having an inner wall made of a hydrophobic material.

In this embodiment, the introduction holes 60 can have a relatively large inner diameter at the surface of the channel base 59 facing the channel cover 13, and therefore it is possible to dispense a liquid into the reaction containers 5 at a lower injection pressure as compared to a case where the introduction holes have a uniform inner diameter.

Each of the embodiments shown in FIGS. 12 and 13 has the air vent channels 5a and the airspaces 5b, but the air vent channels may be omitted.

Although some embodiments of the reaction container plate according to the present invention have been described above, the present invention is not limited thereto and various changes may be made to the shape, material, structure, and number of each of the parts within the scope of the present invention as defined by the appended claims.

For example, in the embodiments described above, the entire channel cover 13 constitutes a flexible portion of the channel cover of the reaction container plate according to the present invention. However, the present invention is not limited to such embodiments, and the channel cover is not particularly limited as long as it has a flexible portion in at least part thereof so that the inside of the introduction channel can be pressurized by biasing the flexible portion toward the channel base to inject a liquid contained in the introduction channel into the reaction container through the introduction hole. An example of such a channel cover is one in which a flexible portion made of a flexible material is provided only at a position corresponding to the introduction hole.

Further, in the embodiments described above, the entire channel base 11 is made of an elastic material. However, the present invention is not limited to such embodiments, and the channel base is not particularly limited as long as it has an introduction hole that prevents a liquid from passing through it when the inside of the introduction channel is at an introduction pressure at which the liquid is introduced into the introduction channel but permits the liquid to pass through it to inject the liquid contained in the introduction channel into the reaction container when the inside of the introduction channel is pressurized so that a pressure in the introduction channel is made higher than the introduction pressure. An example of such a channel base is one in which only the introduction hole and its vicinity are made of an elastic material.

Further, in the embodiments described above, the biasing system 55 is provided to bias the channel cover 13 toward the channel base 11. However, a heating system may be provided instead of the biasing system 55. For example, the second unit 55b shown in FIG. 10 may be changed to a heating system. In this case, as shown in FIG. 10A, an airspace is allowed to be present on the upper side of the internal space of the introduction channel 15 when the mixed liquid 57 is introduced into the introduction channel 15. Then, as shown in FIG. 10B, the first unit 55a is moved toward the reaction container plate 1 to press the channel cover 13 against the channel base 11 at positions around the reaction containers 5. This creates enclosed introduction channel spaces containing the mixed liquid 57 above the reaction containers 5 and the introduction holes 11b. Then, the second unit 55b as a heating system is brought into contact with the channel cover 13 at positions corresponding to the enclosed introduction channel spaces. As a result, the enclosed introduction channel spaces are heated and therefore the pressure in the enclosed introduction channel spaces is increased so that the introduction holes 11b are elastically opened and the mixed liquid 57 is dispensed into the reaction containers 5.

Further, in the embodiments described above, the container base 3 is constituted from one part, but may be constituted from two or more parts.

The reagent contained in the reaction containers 5 may be a dry reagent.

The sample container 17 and the reaction containers 5 do not always need to previously contain a reagent.

The channel base 11 does not always need to have projections 11a.

Further, in the embodiments described above, the air vent channels 5a are connected to the drain space 15c through the airspaces 5b. However, the present invention is not limited to such embodiments, and the air vent channel is not particularly limited as long as it can sufficiently suppress an increase in the pressure in the reaction container caused by injection of a liquid into the reaction container. It is to be noted that the air vent channel is preferably cut off from an external atmosphere or hermetically sealable to prevent the entry of foreign matter from the outside of the reaction container plate and the contamination of an environment outside the reaction container plate caused by the leakage of a liquid.

The container base 3 may further have a gene amplification container for performing a gene amplification reaction. For example, any one of the reagent containers 19 and 21 may be used as a gene amplification container as long as it is empty.

Further, the reaction containers 5 may previously contain a reagent for gene amplification reaction to perform a gene amplification reaction in the reaction containers 5.

In a case where a liquid to be introduced into the introduction channel 15 contains a gene, the reaction containers 5 may contain a probe that reacts with the gene.

INDUSTRIAL APPLICABILITY

The present invention can be applied to various measurements of chemical reactions and biochemical reactions.

What is claimed is:

1. A reaction container plate comprising:
a container base constituted from a substrate including a plurality of reaction containers each having an opening on a surface thereof;
a channel base provided on the surface of the container base to cover the reaction containers and having a plurality of introduction holes each provided above and positioned at the respective reaction container so as to penetrate from a top surface to a back surface thereof; and
a channel cover having a hollow space on a surface thereof and provided on the channel base so that the surface having the hollow space faces the channel base to form only one introduction channel constituted from the hollow space and the top surface of the channel base, the introduction channel being configured to pass above all the introduction holes,
wherein the introduction channel is hermetically sealable,
wherein each of the introduction holes has such an inner diameter that prevents a liquid from passing through it when an inside of the introduction channel is at an introduction pressure at which the liquid is introduced into the introduction channel but permits the liquid to pass through it to inject the liquid contained in the introduction channel into the respective reaction container when the inside of the introduction channel is pressurized so that a pressure in the introduction channel is made higher than the introduction pressure, and
wherein the channel cover has a plurality of flexible portions each having a recess provided in the surface thereof facing the channel base, the recess being arranged to correspond to each of the introduction holes,
the flexible portions being pressed from above toward the channel base to pressurize the inside of the introduction channel to inject the liquid contained in the introduction channel into the reaction containers through the introduction holes.

2. The reaction container plate according to claim 1, further comprising an air vent channel provided so as to communicate with the reaction containers.

3. The reaction container plate according to claim 2, further comprising a hermetically-sealable drain space provided at a position other than a position, at which the reaction containers are provided, so as to be connected to the introduction channel, wherein the air vent channel is connected to the drain space.

4. The reaction container plate according to claim 1, wherein the introduction hole has a narrow portion whose inner diameter is smaller than that of the introduction hole measured at the top surface of the channel base facing the channel cover.

5. The reaction container plate according to claim 4, wherein the narrow portion of the introduction hole has an inner diameter of 1 μm to 2 mm.

6. The reaction container plate according to claim 1, wherein the channel base has a plurality of projections each projecting from a surface thereof facing the reaction container plate toward an inside of each of the reaction containers, and wherein each of the projections has a proximal end and a distal end narrower than the proximal end and each of the introduction holes is provided so as to pass through each of the projections.

7. The reaction container plate according to claim 1, wherein at least a portion including the introduction hole and its vicinity in the channel base is formed from an elastic member so that the introduction hole is elastically closed enough to prevent the passage of a liquid when the inside of the introduction channel is at the introduction pressure, and is elastically opened enough to permit the passage of the liquid when the inside of the introduction channel is pressurized so that a pressure in the introduction channel is made higher than the introduction pressure.

8. The reaction container plate according to claim 1, wherein the container base has a sample container for containing a sample liquid.

9. The reaction container plate according to claim 8, wherein the sample container is hermetically sealed with an elastic member penetrable with a dispensing tool having a sharp tip to form a through hole elastically closable by pulling out the dispensing tool.

10. The reaction container plate according to claim 9, wherein, the sample container is configured to hold a liquid for sample pretreatment or a reagent.

11. The reaction container plate according to claim 1, wherein the container base has one or more reagent containers configured to hold a reagent for use in the reaction of a sample liquid and sealed with a film, or one or more reagent containers having a cap openable and closable to inject the reagent.

12. The reaction container plate according to claim 1, wherein the reaction containers are configured to perform at least any one of a color reaction, an enzyme reaction, a fluorescence reaction, a chemiluminescence reaction, and a bioluminescence reaction.

13. The reaction container plate according to claim 1, wherein the container base has a gene amplification container configured to perform a gene amplification reaction.

14. The reaction container plate according to claim 8, further comprising a syringe for performing one or both of stirring of a liquid contained in the sample container and introduction of a liquid contained in the sample container into the introduction channel.

15. The reaction container plate according to claim 14, further comprising a switching valve for connecting the syringe to the introduction channel or the sample container.

16. The reaction container plate according to claim 15, wherein the syringe is configured to stir a liquid contained in the sample container, introduce a liquid contained in the sample container into the introduction channel or the reagent container, and/or introduce a liquid contained in the reagent container into the introduction channel.

17. The reaction container plate according to claim 16, further comprising a switching valve for connecting the syringe to the introduction channel, the sample container, or the reagent container.

18. The reaction container plate according to claim 15, wherein the switching valve is a rotary valve.

19. The reaction container plate according to claim 18, wherein the rotary valve has a port connected to the syringe at a rotation center thereof, and wherein the syringe is arranged on the rotary valve.

20. The reaction container plate according to claim 1, wherein the reaction containers are configured to measure a sample containing a gene, and wherein the reaction containers are configured to perform a gene amplification reaction.

21. The reaction container plate according to claim 1, wherein the container base is made of an optically-transparent material to perform optical measurement from a bottom side of the reaction containers.

22. The reaction container plate according to claim 1, wherein a liquid introduced into the introduction channel contains a gene, and each of the reaction containers contains a probe that reacts with the gene.

23. Reaction processing equipment for handling a reaction container plate comprising the reaction container plate of claim 1 and a biasing system for biasing the flexible portion of the channel cover toward the channel base.

* * * * *